United States Patent [19]

Lewy et al.

[11] Patent Number: 5,420,152

[45] Date of Patent: * May 30, 1995

[54] METHODS OF TREATING CIRCADIAN RHYTHM DISORDERS

[75] Inventors: Alfred J. Lewy; Robert L. Sack, both of Portland, Oreg.

[73] Assignee: State of Oregon, Acting by and Through the Oregon State Board of Higher Education on Behalf of the Oregon Health Sciences University, a non-profit organization, Portland, Oreg.

[*] Notice: The portion of the term of this patent subsequent to Sep. 7, 2010 has been disclaimed.

[21] Appl. No.: 77,426

[22] Filed: Jun. 15, 1993

Related U.S. Application Data

[60] Division of Ser. No. 842,723, Feb. 25, 1992, Pat. No. 5,242,941, which is a continuation of Ser. No. 621,866, Dec. 4, 1990, abandoned.

[51] Int. Cl.$^6$ ............................................. A61K 31/40
[52] U.S. Cl. ............................................. 514/419
[58] Field of Search ............................... 514/415, 419

[56] References Cited

U.S. PATENT DOCUMENTS

| 4,600,723 | 7/1986 | Short et al. | 514/416 |
| 4,665,086 | 5/1987 | Short et al. | 514/416 |

Primary Examiner—Raymond Henley, III
Assistant Examiner—Phyllis G. Spivack
Attorney, Agent, or Firm—Allegretti & Witcoff, Ltd.

[57] ABSTRACT

A method for treating circadian rhythm disorders is described. The method involves the administration of melatonin from about 6 hours to about 19 hours prior to when the normal sleep phase should begin, depending on whether a phase advance shift in circadian rhythms or a phase delay shift is desired. This is typically from about 4 hours to about 17 hours prior to the time of endogenous melatonin onset.

3 Claims, 6 Drawing Sheets

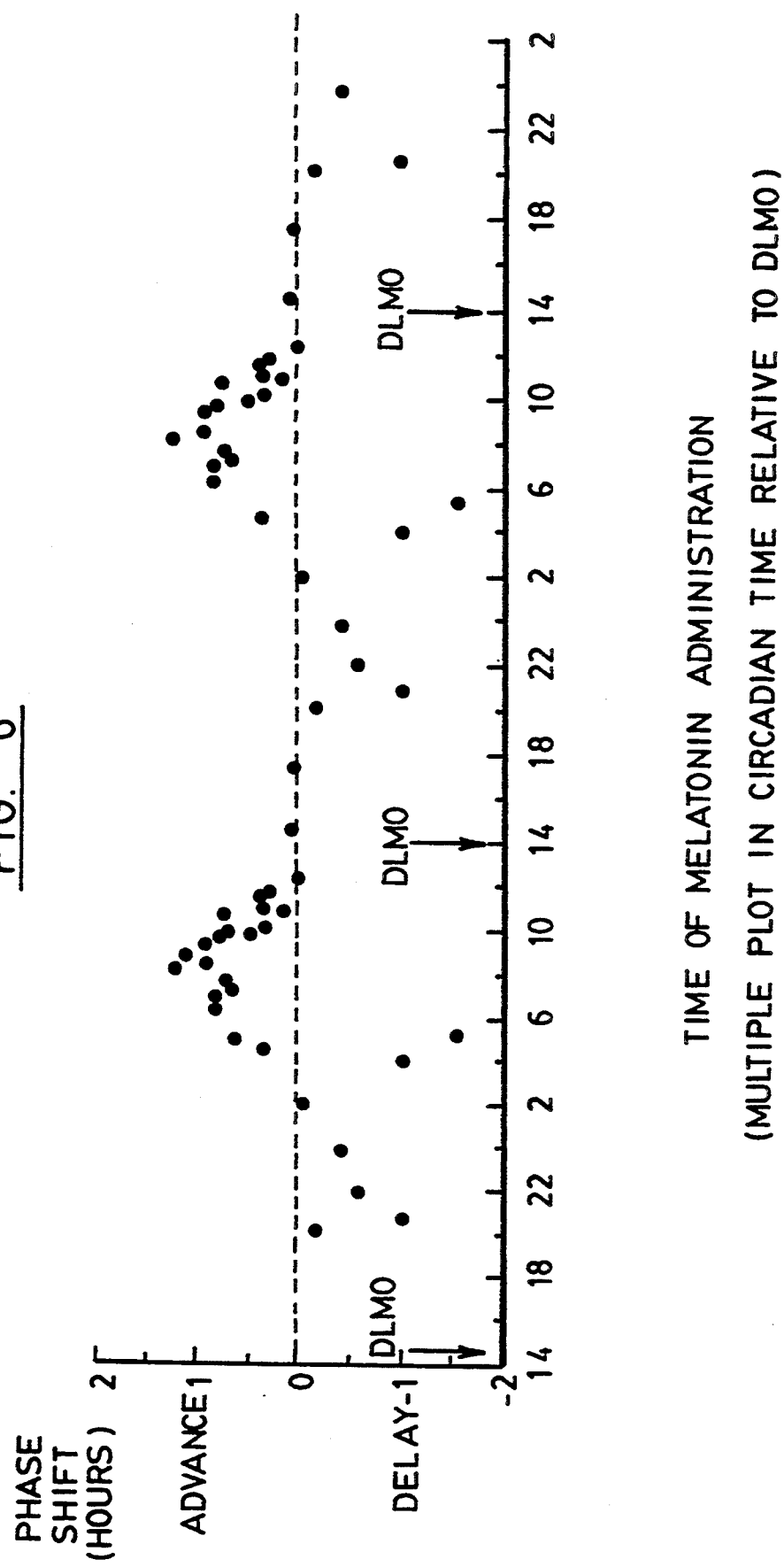

METHODS OF TREATING CIRCADIAN RHYTHM DISORDERS

This invention was made with government support under MH 40161 and MH 00703 awarded by the National Institutes of Health. The government has certain rights in the invention.

BACKGROUND OF THE INVENTION

This application is a divisional application of U.S. patent application Ser. No. 07/842,723, filed on Feb. 25, 1992, now U.S. Pat. No. 5,242,941, issued on Sep. 7, 1993, which in turn was a continuation application of U.S. patent application Ser. No. 07/621,866, filed on Dec. 4, 1990, now abandoned.

1. FIELD OF THE INVENTION

The field of the invention disclosed in this application relates to the regulation of circadian rhythms in humans, and to the synchronization of circadian rhythms with the external environment. Specifically, this invention describes a method to achieve a chronobiologic (circadian phase-shifting) effect in humans. In particular, this invention relates to the reestablishment of synchrony between a human's endogenous biological circadian rhythm and the external environment (including the sleep-wake cycle) after its disruption in any of a number of ways. The invention further describes a method to specifically advance or delay the onset of a specific circadian rhythm in a human.

2. BACKGROUND OF THE RELATED ART

The phenomenon of circadian rhythms in biology is well known, and circadian rhythms are exhibited by all eukaryotic plants and animals, including man. Biological rhythms are periodic fluctuations in biological properties over time; these include circadian as well as seasonal variations. Circadian, or approximately 24-hour, rhythms include the production of biological molecules such as hormones, the regulation of body temperature, and behaviors such as wakefulness, sleep and periods of activity. In nature, circadian rhythms are closely tied to environmental cues that impose a 24 hour pattern on many of these fluctuations. Experimental inquiry has established that when these cues are absent, most circadian rhythms have a periodicity of approximately 25 hours. Circadian rhythms that are not regulated by environmental cues are said to be free-running. The regulation of circadian rhythms by signals from the environment is said to involve entrainment of the circadian rhythms. The environmental signals that effect entrainment have been termed zeitgebers, an example of which is the light-dark cycle.

It is thought in the art that the control of circadian rhythms in mammals is mediated by a portion of the brain called the superchiasmatic nuclei (SCN). One of the major circadian rhythms, the pattern of wakefulness and sleep, is mediated by a feedback loop involving the retina, the SCN and the pineal gland. The pineal gland is primarily responsible for the production of melatonin, or N-acetyl-5-methoxytryptamine. Melatonin is believed to be the physiological mediator of sleep and wakefulness in mammals.

The disruption of circadian rhythms can result in a number of pathophysiological states in humans; the most common of these is jet lag. The use of melatonin to ameliorate the effects of jet lag has been described in the prior art.

U.S. Pat. Nos. 4,665,086 and 4,600,723 teach the use of melatonin to alleviate the symptoms of jet lag. These patents teach the use of 1–10 mg of melatonin, taken at destination bedtime, and again upon premature awakening in the middle of the night. A number of examples are disclosed in these patents, all of which involve travelers who take these doses of melatonin at destination bedtime and report the alleviation of the symptoms of jet lag.

Without wishing to be bound to this hypothesis, the present inventors believe that U.S. Pat. Nos. 4,665,086 and 4,600,723 are mistaken when they describe their use of exogenous melatonin as resulting in restoration of a circadian rhythm. Rather, the administration of exogenous melatonin taught by these patents should merely reinforce the (usual) rise in endogenous melatonin which occurs near the time of sleep onset. It is known that melatonin in high doses increases tiredness and the tendency to sleep (see Arendt et al. Neurosci. Lett. 45: 317-325, 1984; Arendt et al. CIBA Found. Symp. 117: 266-283, 1986). The present inventors believe that the effect described in U.S. Pat. Nos. 4,665,086 and 4,600,723 arises mainly from the soporific, hypnotic and sleep-inducing properties of melatonin administered at high doses, and that following the teachings of these patents would result in little, if any, change in the circadian rhythms of endogenous melatonin production.

Arendt et al. Ergonomics 30:1379-1393 (1987) disclose the administration of melatonin to alleviate jet lag. Exogenous melatonin is administered orally from 4 to 6 hours prior to the human's normal bedtime and taken upon awakening in the middle of the night. This schedule of melatonin administration was reported subjectively both to improve sleep quality and decrease sleep latency and to promote a more rapid reestablishment of the circadian rhythms of endogenous melatonin production. The present inventors believe that the data presented do not support the latter conclusion. No prior art references known to the present inventors teach melatonin administration more than 6 hours prior to the patient's normal bedtime to alleviate jet lag in a human. No prior art references known to the present inventors relate exogenous melatonin administration to the time interval between such administration and the time of endogenous melatonin onset in humans.

Armstrong et al. Experientia 45:932-938 (1989) disclose that in rats the effects of exogenous melatonin administration on the circadian rhythm of the sleep/wake cycle depends on the time of administration relative to the sleep/wake cycle, and that the effect was greatest when exogenous melatonin was administered several hours before the effective start of the nocturnal activity cycle. However, these authors were unable to demonstrate phase-delay shifts or a phase-response curve (PRC); that is, they did not relate the timing of exogenous melatonin administration to the time of the endogenous melatonin onset.

Gwinner and Benzinger J. Comp. Physiol. 126: 123-129 (1978) teach that daily injections of melatonin can entrain the activity/rest cycle in birds.

Underwood J. Pineal Res. 3:187-196 (1986) disclosed a PRC for melatonin in the lizard *Sceloporus occidentalis*.

Mallo et al. Acta Endocrinol. 119: 474–480 (1988) teach the adminstration of 8 mg of melatonin to humans, one hour before bedtime over a course of four days, results in a slight phase advance three days after cessation of the melatonin treatment.

Entrainment and regulation of the melatonin circadian rhythm has thus been demonstrated in a number of animal species. The present inventors are the first to disclose a PRC for melatonin in a human, and perhaps in any mammalian species. The ability to effect an actual change in phase of the circadian rhythm would be useful for the alleviation of a number of circadian rhythm related disorders, as will be further discussed in the embodiments below. This application discloses a method to advance or delay the onset of the production of endogenous melatonin, and hence actually affect the regulation of an endogenous circadian rhythm in man.

SUMMARY OF THE INVENTION

This invention relates to a method for achieving a chronobiologic (phase-shifting) effect in a human. This effect is achieved by regulation of a human's circadian rhythm. Specifically, the circadian phase-shifting effect is achieved by the administration of exogenous melatonin, which naturally occurs in the human only during the night. The timing of the nighttime onset of melatonin production in a particular individual may be expected to vary from person to person. The circadian rhythm of melatonin production in a human is entrained principally by the (bright) light-dark cycle and reflects a variety of other biological properties which vary with a circadian rhythm. The method of the invention entails the phase-shifting of the circadian rhythm by administration of exogenous melatonin. More specifically, the method of the invention involves the administration of a particular dosage of melatonin to the human. The particular dosage is lower than dosages taught by others, and is designed to achieve melatonin levels which are substantially equal to physiological levels in the human. Further, the method of the invention relates to the timing of the administration of the dosage of melatonin to the human. The timing of this dosage in the human is described to specifically phase-shift the circadian rhythm of endogenous melatonin production. The method described in the invention can be used to advance or delay the phase of the circadian rhythm of melatonin production in the human. In this way, the present invention is able to alleviate jet lag and other circadian rhythm disorders of both the phase-delay and the phase-advance types.

The present inventors have discovered that the time of administration of exogenous melatonin relative to the time of endogenous melatonin onset is critical to the production of the appropriate phase-shifting effect. The time of administration of exogenous melatonin must be carefully set relative to the time of endogenous melatonin onset, preferably from more than 4 hours to about 8 hours before endogenous melatonin onset when a phase advance is desired, and about 9 hours to about 17 hours before endogenous melatonin onset when a phase-delay is desired. Since the endogenous melatonin onset typically occurs about 2 hours prior to when the normal sleep phase should begin, exogenous melatonin should be preferably administered from more than 6 hours to about 10 hours prior to the commencement of the patient's normal sleep phase when a phase-advance is desired, and about 11 hours to about 19 hours prior to the commencement of the patient's normal sleep phase when a phase-delay is desired. The preferred time of administration of exogenous melatonin for a particular individual human will be unique, depending on the individual's time of endogenous melatonin onset, which can vary markedly from individual to individual (between 7 PM to 11 PM for most individuals). An increase of at least 15-30 minutes of phase shifting will occur for each day of exogenous melatonin treatment administered as described in a preferred embodiment below.

BRIEF DESCRIPTION OF THE DRAWINGS

FIGS. 5 and 6 disclose the experimental results of Example 5.

DETAILED DESCRIPTION OF THE PREFERRED EMBODIMENTS

Figure 1:
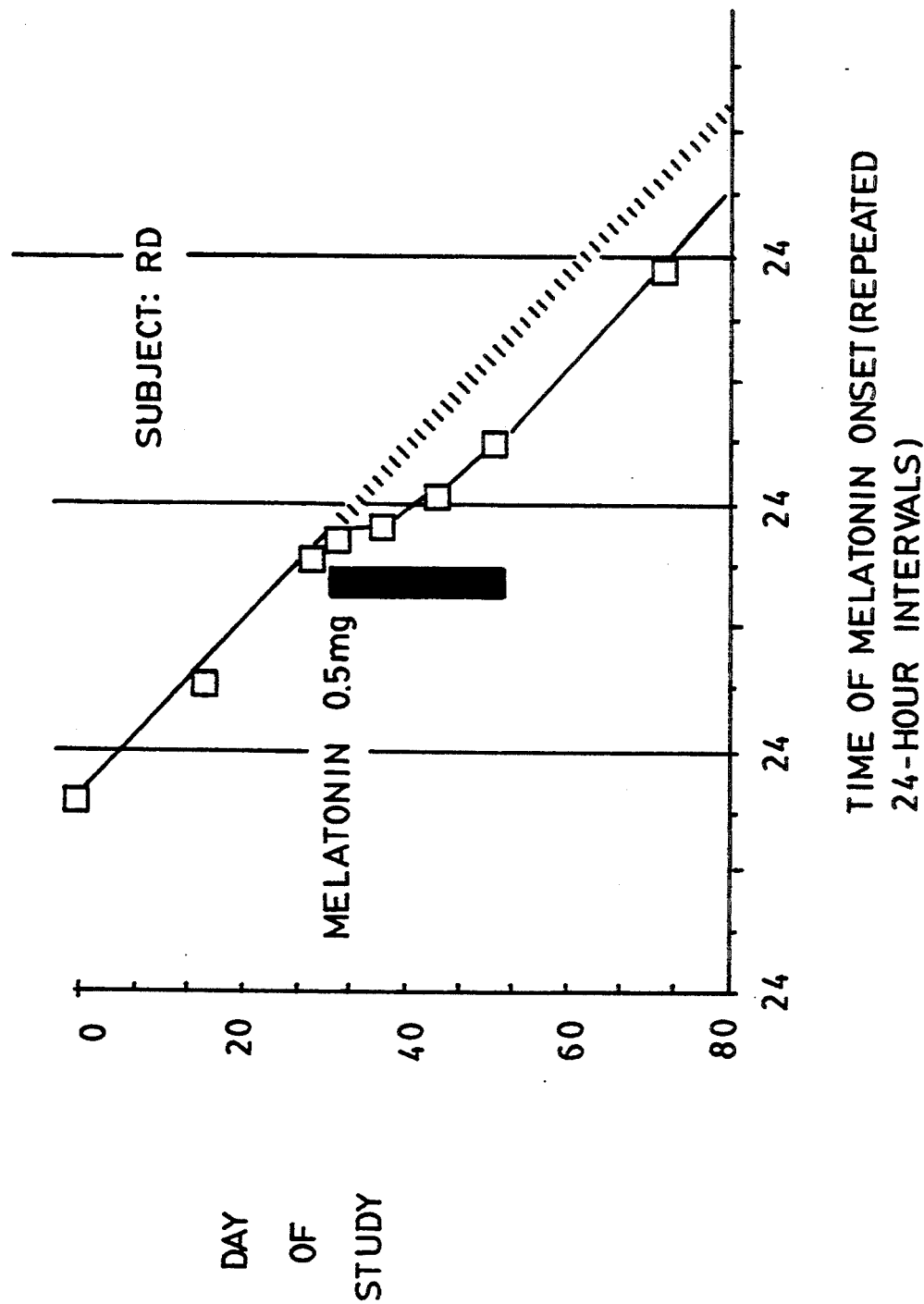
FIG. 1 discloses the experimental results of Example 2.

The amount of melatonin administered to the human patient should be sufficient to achieve the desired circadian phase-shifting effect. In a preferred embodiment of this invention, a dosage of about 0.25 mg to about 0.75 mg, most preferably about 0.50 mg, of exogenous melatonin is used to effect the desired change in phase of the circadian rhythms of endogenous melatonin production. In a preferred embodiment, the total dose of melatonin is given in two or more smaller portions to the human patient over an interval of about two hours if the person is awake. One dose time is preferred if the person is asleep.

Pharmaceutical quality melatonin is commercially available. The dosage of melatonin may be administered orally, by injection, via a transdermal patch or by implantation of a reservoir designed to release a steady dosage of melatonin over time. In a preferred embodiment of this invention, melatonin is administered orally.

In a preferred embodiment of this invention, a phase advance in the circadian rhythms of endogenous melatonin production is effected by the administration of an amount of exogenous melatonin sufficient to achieve the phase advance from more than 6 hours to about 10 hours, preferably from about 7 to about 10 hours, most preferably about 8 hours, before the human's normal sleep phase should begin. This is typically from about 4 hours to about 8 hours, most preferably about 6 hours, before the patient's endogenous melatonin onset.

A phase delay in the circadian rhythm of endogenous melatonin production is effected by the administration of an amount of exogenous melatonin sufficient to achieve the phase delay from about 11 to about 19 hours, most preferably from about 12 to about 16 hours, prior to when the human's normal sleep phase should begin. This is typically from about 9 hours to about 17 hours, most preferably from about 10 to about 14 hours, before the patient's endogenous melatonin onset.

A modification of the method of Lewy and Markey (Science 201:74 1-3, 1978) may be used to determine the time of onset of the patient's endogenous melatonin production. The preferred use of this method is taught in Example 1.

The present invention may be used in, but is not limited to, the following situations to achieve chronobiologic effects and/or to alleviate circadian rhythm disorders: jet lag; shift work; astronauts in orbit around the Earth, on missions in space to the Earth's moon or to the planets or out of the known solar system, or in training for such missions; submariners, or persons confined for research, exploration or industrial purposes below the seas; miners, explorers, spelunkers, researchers or those confined beneath the Earth; psychiatric patients; insomniacs; the comatose, or those who need to be maintained in a state of unconsciousness for medical, psychiatric or other reasons; medical residents, nurses, firemen, policemen or all those whose duties require alertness and wakefulness at evening or nighttime hours, or those deprived of sleep for various periods because of their duties or responsibilities; the infantry, or other members of the armed forces whose duties require extreme levels of alertness and wakefulness, and who may be sleep deprived in the performance of these duties; the blind or sight-impaired, or all those whose ability to distinguish differences in light and dark may be permanently or temporarily impaired; residents of the far North or Antarctica, or all those who live in a climate or climates that possess abnormal amounts of light or darkness; those suffering from seasonal affective disorder, or other forms of depression; the aged; the sick, or all those who require dosages of medication at appropriate times in the circadian cycle; and animal breeders, for use in controlling circadian time.

The following examples describe certain specific embodiments of the invention. However, many additional embodiments not described herein nevertheless fall within the spirit and scope of the present invention and claims.

EXAMPLE 1

Detection of Melatonin Levels in Human Plasma

Prior to collection of human blood, subjects are kept in dim light for about 5 hours (usually between 6 PM and 11 PM). An intravenous line or heparin lock is inserted in a forearm vein and 5 ml of blood drawn every 30 minutes between 7 PM and 11 PM. The blood samples are centrifuged for 5 minutes at 1000 g and 4° C., and the plasma aspirated into a silanized glass or plastic tube. Samples are assayed immediately or frozen for later analysis. To a 1 ml aliquot of such plasma was added 15–40 picograms of N-acetyl-5-methoxy($\alpha$, $\alpha$, $\beta$, $\beta$-D$_4$)tryptamine as a chromatographic control. An equal volume of normal saline is added and the mixture gently shaken with 10 volumes of petroleum ether. The organic phase is removed, and melatonin and the added N-acetyl-5-methoxy($\alpha$, $\alpha$, $\beta$, $\beta$-D$_4$)tryptamine control extracted from the aqueous phase with 10 volumes of chloroform. The aqueous phase is then discarded, and the chloroform evaporated to dryness.

The dried extract containing melatonin and the added N-acetyl-5-methoxy($\alpha$, $\alpha$, $\beta$, $\beta$-D$_4$)tryptamine control is dissolved in 0.4 ml of anhydrous acetonitrile. The melatonin and the added N-acetyl-5-methoxy($\alpha$, $\alpha$, $\beta$, $\beta$-D$_4$)tryptamine control are then derivatized by the addition of 25 $\mu$l of pentafluoroproprionic acid anhydride and 0.5 ml of a solution of 5% trimethylamine in anhydrous benzene and reacted at 100° C. for 10 minutes. The reaction products are washed sequentially with 1 ml water and 1 ml 5% ammonium hydroxide. The mixture is centrifuged briefly at 13,000 g and the organic phase withdrawn and evaporated to dryness under nitrogen. The dried extract is partitioned between 0.5 ml acetonitrile and 1 ml hexane by vigorous mixing followed by centrifugation. The hexane layer is removed and the acetonitrile evaporated to dryness under nitrogen. This partitioning step is performed two times for each sample. The dried extract is re-patitioned for storage. The derivatives are stable and can be stored at −20° C. for several weeks.

The amount of melatonin present in each sample is determined by analysis using a gas chromatograph-mass spectrometer (GC-MS). Before injection onto the GC column, the dried derivatives are dissolved in 15 $\mu$l of ethyl acetate. Approximately half this volume was applied to a 30 m×25 $\mu$m fused silica capillary column [0.15 micron film thickness with a 1 m retention gap (DB-225, J&W Scientific, Folsom Calif.)]. The oven is programmed from 60° C. to 240° C. (at 25.5° C./min) with helium as carrier gas (10 psi head pressure) and methane used as make-up gas (ionizer, 0.6 torr). Derivatized melatonin and the added N-acetyl-5-methoxy($\alpha$, $\alpha$, $\beta$, $\beta$-D$_4$)tryptamine derivatized control are found to elute from the column after 10–14 minutes. Mass spectrographic analysis of the column eluate is then performed. Mass spectra are recorded using a Finnigan 4000-GC-CI analyzer and INCOS data system. A Finnigan PPIMCI electron multiplier with 3 kV conversion was used, signal referenced to ground. The relative signals of melatonin and the added N-acetyl-5-methoxy($\alpha$, $\alpha$, $\beta$, $\beta$-D$_4$)tryptamine control are detected at m/e (mass/charge) ratios of 320 and 323, respectively. The amount of melatonin present in any unknown sample can be determined by comparison of the ratio of the intensities of these signals to a standard curve, prepared as described using known amounts of melatonin and added N-acetyl-5-methoxy($\alpha$, $\alpha$, $\beta$, $\beta$-D$_4$)tryptamine control.

EXAMPLE 2

Without light perception, blind people often have circadian rhythms that free run with a period greater than 24 hours. We have been successful in phase-shifting a free running circadian rhythm in at least one blind subject by administering 0.5 mg doses of melatonin orally.

A blind subject whose circadian rhythms were free-running was placed on a three-week regimen to phase-shift his circadian rhythms using administration of exogenous melatonin. The subject was given 0.25 mg of melatonin orally at 1900 and 2100 hours (clock time) every day for three weeks. The effect of exogenous melatonin administration on the time of endogenous melatonin onset is disclosed in FIG. 1. The cumulative phase advance seen in this subject is equivalent to the phase advance obtained when a much higher dose (5 mg) was used. These results confirm that exogenous melatonin administration can effect a phase advance in a human.

EXAMPLE 3

The effect of exogenous melatonin administration on circadian rhythm of sighted people was tested. Eight normal subjects were treated in a two-week protocol, similar to the one used in Example 2. During the first week, the subjects were given a placebo at 1700 and 1900 hours and the time, extent and amount of dim light melatonin onset (DLMO) was measured as described in Example 1. During the second week, subjects were given placebo at 1700 and 1900 hours for two days, and then melatonin was administered in two doses of 0.25 mg at 1700 and 1900 hours for 4 days and the subjects' DLMO determined.

Figure 2:
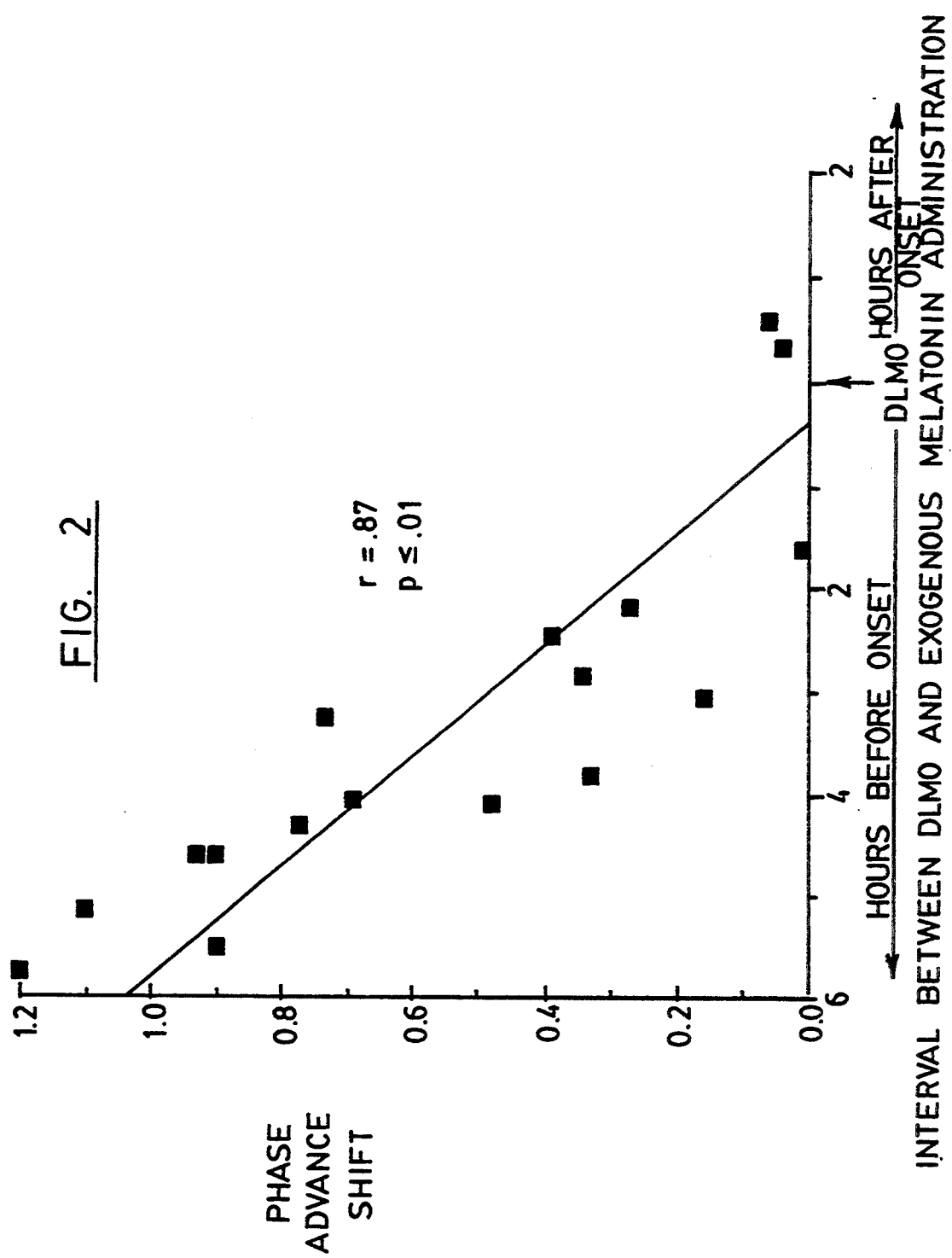
FIG. 2 discloses the experimental results of Example 3.

Seventeen trials were conducted on the eight subjects. The results of this study are shown in FIG. 2. The Figure shows the relationship between the degree of phase shift obtained and the interval between the time of administration of exogenous melatonin and the endogenous DLMO. This interval is also known as the phase angle difference. The earlier the exogenous melatonin is administered the greater is the magnitude of the phase advance; that is, there is a positive correlation between the extent of phase advance achieved by exogenous melatonin administration and the time interval between the time of exogenous melatonin administration and the time of endogenous melatonin onset. These results confirm that exogenous melatonin administration can effect a phase advance in humans, and that the timing of exogenous melatonin administration relative to the onset of endogenous melatonin is critically important for phase shifting circadian rhythms.

EXAMPLE 4

Figure 3:
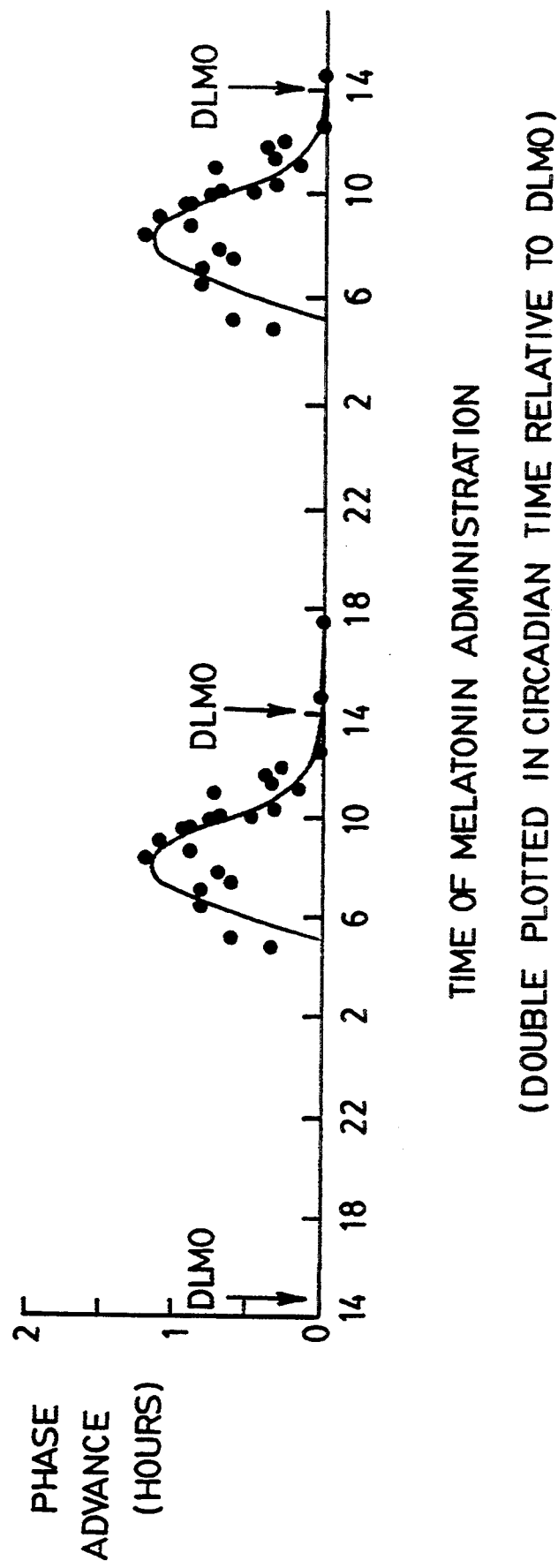
FIGS. 3 and 4 disclose the experimental results of Example 4.
Figure 4:
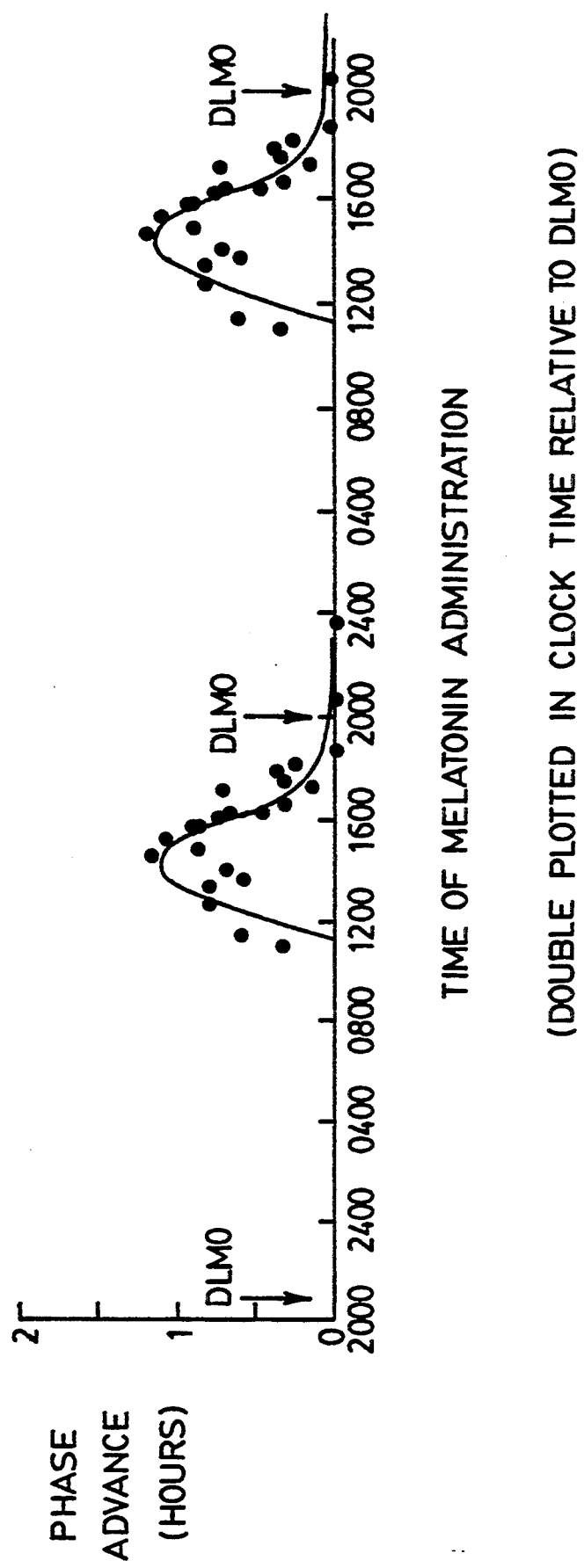

The effect of exogenous melatonin treatment administered at earlier times relative to the endogenous melatonin rhythm was tested in sighted people. Twenty-four trials were conducted in the eight normal subjects who were treated in a two-week protocol similar to the one used in Example 3. During the first week, placebo was administered and the time, extent and amount of dim light melatonin onset (DLMO) was determined. Subsequently in the second week, melatonin was administered at various times prior to the time of endogenous melatonin onset, and the subjects' endogenous melatonin onset was determined. The results of this study are shown in FIGS. 3 and 4. FIG. 3 expresses the results in terms of circadian time [assuming the DLMO occurs at (CT) 14], and FIG. 4 expresses the same results in terms of military time [assuming that DLMO is at 2000 hours (8 PM)]. These results show that the maximum degree of phase advance in the onset of endogenous melatonin occurred after administration of exogenous melatonin at circadian time (CT) 8, or 6 hours prior to the normal time of melatonin onset in the subjects (CT 14). This corresponds to a time of about 8-10 hours before normal bedtime in these subjects. The observed phase advance declines rapidly when exogenous melatonin is administered prior to CT 8. Between CT 8 and CT 14, the decline in the degree of phase advance is linear and proportional to the phase angle between time of administration and time of endogenous onset. Minimal effect, if any, on the circadian rhythm of endogenous melatonin onset is seen when the time of administration of exogenous melatonin coincides with the normal time of onset of endogenous melatonin (CT 14).

EXAMPLE 5

Figure 5:
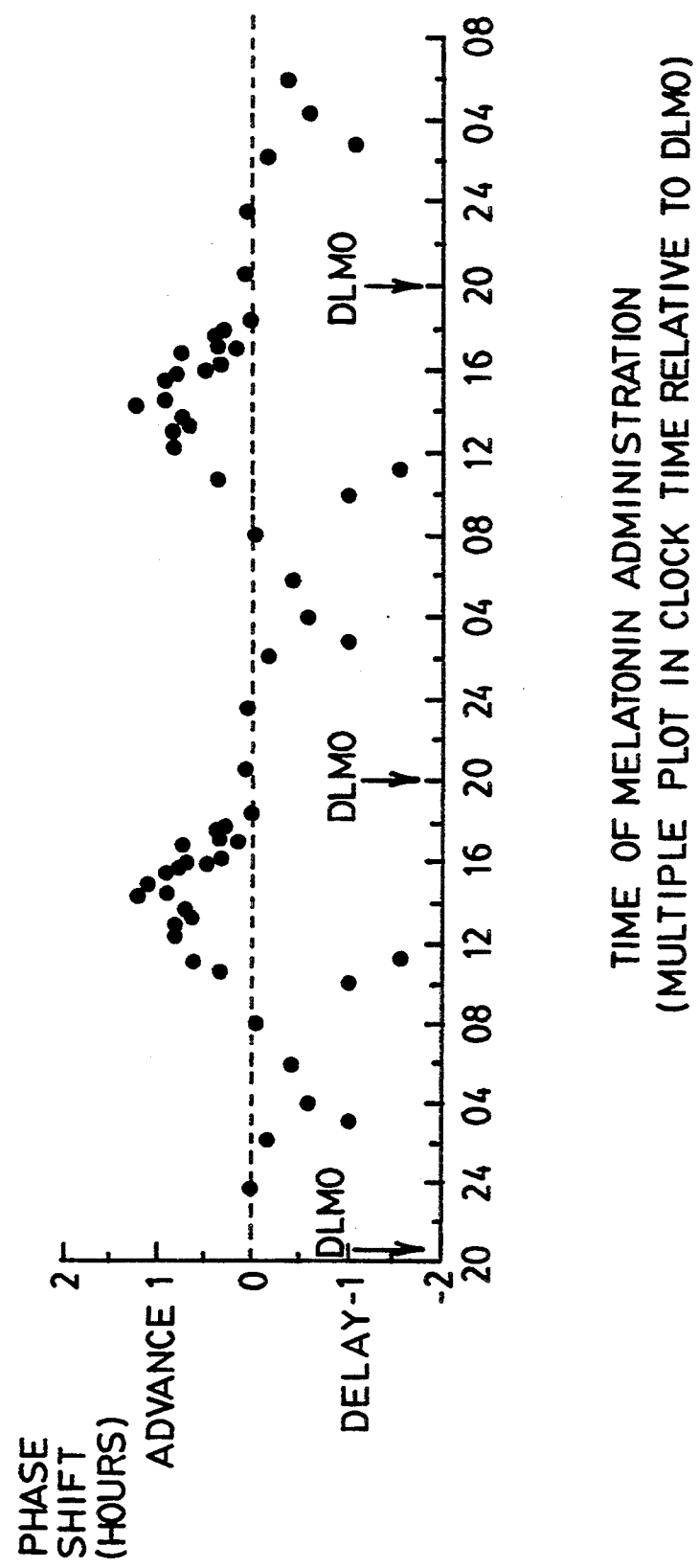

Experiments to investigate the use of exogenous melatonin to effect a phase delay were also performed. These experiments followed the protocol explained in Example 4; however, the time of administration of melatonin was altered. A total of 30 trials using nine subjects were performed. The results of this experiment are shown in FIGS. 5 and 6. In this regime, exogenous melatonin was administered about 11-19 hours before normal bedtime. It was found that administration of exogenous melatonin from about 9 hours to about 17 hours before the endogenous melatonin onset resulted in the greatest degree of phase delay in the onset of endogenous melatonin production.

We claim:

1. A method for achieving a phase-shifting effect in a human comprising the following steps:
   a) determining the time of the human's endogenous melatonin onset; and
   b) administering an amount of melatonin to the human at a specific time prior to the human's endogenous melatonin onset, the time being from about 4 to about 12 hours prior to the human's endogenous melatonin onset time, and the amount of melatonin being sufficient to achieve the phase-shifting effect in the human, said amount being less than 1 mg.

2. The method of claim 1 wherein the phase-shifting effect is a phase advance and the melatonin is administered at about 4 hours to about 8 hours prior to the human's endogenous melatonin onset.

3. The method of claim 1 wherein the phase-shifting effect is a phase delay and the melatonin is administered at about 9 hours to about 12 hours prior to the human's endogenous melatonin onset.

* * * * *